United States Patent [19]

Siskin et al.

[11] 4,064,189

[45] Dec. 20, 1977

[54] PROCESS FOR REACTING PARAFFINIC HYDROCARBONS UTILIZING HYDROGEN, METAL PENTAFLUORIDE AND HYDROGEN HALIDE

[75] Inventors: Michael Siskin, Maplewood; Joseph J. Porcelli, Scotch Plains, both of N.J.

[73] Assignee: Exxon Research & Engineering Co., Linden, N.J.

[21] Appl. No.: 756,536

[22] Filed: Jan. 3, 1977

Related U.S. Application Data

[63] Continuation-in-part of Ser. No. 586,176, June 12, 1975, Pat. No. 4,025,577.

[51] Int. Cl.$^2$ ............................................. C07C 9/00
[52] U.S. Cl. .......................... 260/676 R; 260/683.51; 260/683.68; 260/666 P
[58] Field of Search ................... 260/683.47, 683.51, 260/676 R, 683.68, 666 P

[56] References Cited

U.S. PATENT DOCUMENTS

| | | | |
|---|---|---|---|
| 3,678,120 | 7/1972 | Bloch | 260/683.47 |
| 3,809,728 | 5/1974 | Kemp et al. | 260/683.47 |
| 3,819,743 | 6/1974 | McCaulay | 260/676 |
| 3,903,196 | 9/1975 | Kemp | 260/683.51 |
| 3,979,476 | 9/1976 | Kemp | 260/683.47 |
| 4,025,577 | 5/1977 | Siskin et al. | 260/683.51 |

*Primary Examiner*—George Crasanakis
*Attorney, Agent, or Firm*—John W. Ditsler

[57] ABSTRACT

High octane alkylates are prepared by selectively alkylating paraffinic hydrocarbons with other paraffinic hydrocarbons at alkylation conditions in the presence of hydrogen and of a catalyst comprising a metal pentafluoride selected from the group consisting of tantalum pentafluoride, niobium pentafluoride and mixtures thereof and a hydrogen halide. The product obtained is a mixture containing primarily $C_4$–$C_6$ isomerized paraffins.

17 Claims, No Drawings

PROCESS FOR REACTING PARAFFINIC HYDROCARBONS UTILIZING HYDROGEN, METAL PENTAFLUORIDE AND HYDROGEN HALIDE

CROSS REFERENCE TO RELATED APPLICATIONS

This application is a continuation-in-part of application Ser. No. 586,176 filed June 12, 1975, which issued as U.S. Pat. No. 4.025,577, the disclosures of which are incorporated herein by reference.

BACKGROUND OF THE INVENTION

The present invention relates, in general, to hydrocarbon conversion processes. More particularly, this invention relates to a process for the selective hydroalkylation of paraffinic hydrocarbons in the presence of a catalyst comprising a metal pentafluoride selected from the group consisting of tantalum pentafluoride, niobium pentafluoride and mixtures thereof and a hydrogen halide, wherein the product thus formed contains primarily $C_4$-$C_6$ isomerized paraffins.

DESCRIPTION OF THE PRIOR ART

The acid catalyzed addition of an alkane to another alkane is well known in the art. Generally, such a catalytic alkylation of paraffins involves the addition of an alkyl cation derived from an isoparaffin containing a tertiary hydrogen to another paraffin followed by selective cleavage to form the alkylate. The process can be used by the petroleum industry to prepare highly branched $C_4$-$C_{12}$ paraffins that are high quality fuels for internal combustion and other engines. The process conditions required and the product composition depend on the particular hydrocarbons involved in the reaction.

Hydrocarbon conversion processes involving the use of metal halide based catalysts have been extensively described in the prior art. For example, U.S. Pats. Nos. 2,683,763 and 2,683,764 disclose that tantalum pentafluoride or columbium (niobium) pentafluoride in combination with hydrogen fluoride can be used to refine hydrocarbon oils or to promote the disproportionation of alkyl-substituted aromatic materials. The patentees also disclose that hydrogen fluoride/tantalum pentafluoride and hydrogen fluroide/columbium pentafluoride are powerful catalysts for isomerization, alkylation, cracking and other reactions of aromatics. More recently, U.S. Pat. Nos. 3,708,533 teaches that high octane alkylates can be produced by contacting paraffinic and/or alkyl substituted aromatic hydrocarbons with olefins in the presence of a catalyst comprising one or more metal halides and a strong Bronsted acid selected from the group consisting of fluorosulfuric acid and trifluoromethanesulfonic acid and mixtures thereof. However, when paraffinic hydrocarbons are selectively alkylated with another paraffin in the presence of hydrogen using the catalyst system of the present invention as described hereinafter, there will result an alkylate of enhanced product quality because of better selectivity to desired alkylate products than that obtained using catalyst systems taught in the prior art.

SUMMARY OF THE INVENTION

Now in accordance with the present invention, it has been discovered that $C_3$-$C_6$ paraffinic hydrocarbons are selectively alkylated with other paraffinic hydrocarbons at alkylation conditions in the presence of hydrogen and of a catalyst comprising a metal pentafluoride selected from the group consisting of tantalum pentafluoride, niobium pentafluoride and mixtures thereof and a hydrogen halide. In general, reaction temperatures may range broadly, i.e. from about $-100°$ to about $-100°$ C., preferably from about $-30°$ to about $-75°$ C., and more preferably from about $-10°$ to about $+60°$ C.

Catalysts of the type described herein have been well known to catalyze alkylation reactions, particularly where the second component is fluorosulfuric acid or trifluoromethanesulfonic acid. It has been suprisingly found, however, that when a hydrogen halide, preferably hydrogen fluoride, is employed in conjunction with hydrogen and a metal pentafluoride, preferably tantalum pentafluoride, niobium pentafluoride or mixtures thereof, the reacion is highly selective to the formation of desirable alkylate products. Thus, according to the present invention, selectivity to $C_4$-$C_{12}$ branched alkylate product (which contains a major portion, preferably primarily $C_4$-$C_6$ isomerized paraffins) is enhanced because the formation of intermediate esters and subsequent polymerization reactions which occur when using either fluorosulfuric acid or trifluoromethanesulfonic acid under similar reaction conditions is minimized. Preferably, the present alkylation process is conducted in the substantial absence of aromatic compounds.

DETAILED DESCRIPTION OF THE INVENTION

The hydrocarbon conversion catalyst referred to herein comprises a metal pentafluoride selected from the group consisting of tantalum pentafluoride, niobium pentafluoride and mixtures thereof and a hydrogen halide. Tantalum pentafluoride is meant to include tantalum pentafluoride as well as other fluoride species, e.g., ions such as $Ta_2F_{11}^-$, $Ta_3F_{16}^-$ and the like, that may be formed when tantalum pentafluoride is mixed with the hydrogen halide and the hydrocarbon reactants. This applies similarly to niobium pentafluoride. Useful hydrogen halides include hydrogen bromide, hydrogen chloride, and hydrogen fluoride. The preferred hydrogen halide catalyst constituent is hydrogen fluoride.

According to the present invention, it has been found that the selectivity to $C_4$-$C_{12}$ branched alkylate is enhanced by use of a hydrogen halide, rather than other acids such as fluorosulfuric and trifluoromethanesulfonic, in combination with a metal halide. This is due primarily to minimizing the formation of intermediate esters, polymerization reactions and the like. While not wishing to be bound by any particular theory, it is believed that such undersirable reactions are minimized because such ester formation does not occur in the presence of a hydrogen halide. As such, acid dilution and consumption due to concomitant self-alkylation, polymerization reactions, etc., i.e., reactions which lead to catalyst degradation, poorer product quality, and excess consumption of the hydrocarbon feedstock, are minimized. Another factor which is believed to contribute to the higher selectivity to $C_4$-$C_{12}$ branched alkylate with the present hydrogen halide containing acid catalyst system is the lower solubility of the unsaturated organic materials, e.g. olefins, in the above-mentioned non-oxygenated acids.

It has also been discovered that the present alkylation process is more efficient when carried out in the substantial absence of aromatic compounds. In the present invention, the aromatic compounds will be readily alkylated to more basic compounds which in turn will dilute the acid catalyst and hence the effectiveness of the catalyst. Thus, although aromatic compounds may be present in the feedstock, it is preferred that the present alkylation process be conducted in their substantial absence, i.e. less than about 1 wt. %.

The effectiveness of the catalyst is related to the molar ratio of hydrogen halide to metal pentafluoride. While relatively minor amounts, i.e. less than equimolar amounts, of hydrogen halide relative to metal pentafluoride will dissolve at least a portion of the metal pentafluoride and thereby effect the reaction, the rate of reaction is inordinately slow. However, the reaction rate, i.e. the yield in a given period of time, will be increased if at least an equal molar amount of hydrogen halide relative to metal pentafluoride is present in the reaction zone. Increasing the mole ratio of hydrogen halide to metal pentafluoride provides additional hydrogen halide so as to dissolve more of the metal pentafluoride and thereby provide an increasing amount of liquid phase catalyst which will favor an increased reaction rate. The effect of increasing amounts of liquid phase catalyst on reaction rate becomes more pronounced when the mole ratio of hydrogen halide to metal pentafluoride is in excess of one and continues as the liquid phase of the catalyst increases. Thus, the mole ratio of hydrogen halide to metal pentafluoride is preferably at least 2:1 and more preferably at least 5:1. The favorable effects mentioned above will ultimately level off as the hydrogen halide dilutes the acidity of the reaction system. Thus depending upon the relative amounts of catalyst constituents used, the catalyst, when no support is employed, may be a homogeneous solution of the metal pentafluoride in the hydrogen halide or a mixture of solid and dissolved metal pentafluoride in hydrogen halide.

The catalyst may be used as the neat liquid, as a diluted solution or as a solid, such as adsorbed on a solid support. If on a support, the catalyst may be used in a fluidized bed, in a molten salt process or suspended in a reaction mixture. With regard to the use of the catalyst in solution, any diluent or solvent may be used that is inert to the catalyst under the particular hydrocarbon conversion reaction conditions. To obtain optimum results, the diluents should be pretreated to remove catalyst poisons such as water and the like. Typical diluents or solvents include sulfuryl chloridefluoride, sulfuryl fluoride, sulfolanes, fluorinated hydrocarbons, Freons, polyfluorinated-polyhalogenated hydrocarbons, mixtures thereof and the like. When a solvent or diluent is used, sufficient amounts are employed to maintain the viscosity of the catalyst mixture at a desired level. The amount of diluent employed can vary appreciably and can range as high as 98 volume % of the catalyst mixture. Preferably, the diluent:catalyst volume ratio may range from about 20:1 to 1:1. Higher dilutions may be desirable, for example, in those reactions that proceed with high exothermicity.

The catalyst may be mixed in the absence of any diluent. The components of the catalyst can be mixed separately, that is preferably in the absence of reactants, or in situ in the presence of reactants. Regarding the order in which the reactants are added, it is preferred to add smaller paraffins to the catalyst, alone or in mixture with the larger paraffin, rather than only larger paraffins to said catalyst.

The catalyst system may be incorporated with a suitable solid carrier or support. Any solid catalyst support may be used that is inert to the catalyst under the reaction conditions. If the support is not inert, the support should be pretreated, such as by heating, chemical treatment or coating, to remove substantially all water and/or hydroxylic sites that might be present. Reactive supports may be rendered inert by coating them with an inert material such as antimony trifluoride or aluminum trifluoride, or by treatment with Freons, fluorine or fluorinating agents such as when hydrogen fluoride is present in the catalyst. Suitable solid supports include fluoride-treated or coated resins such as sulfonated cation exchange resins, fluoride-treated acidic chalcites such as alumina and aluminosilicates and acid-resistant molecular sieves such as faujasite and zeolites, graphite, chromosorb T, Fluoropak 80, etc.

The supported catalyst can be prepared in any suitable manner, such as by conventional methods including dry mixing, coprecipitation or impregnation. In one embodiment, the supported catalyst is prepared by impregnating a suitable deactivated support with a metal pentafluoride such as tantalum pentafluoride and then with a hydrogen halide such as hydrogen fluoride. The weight ratio of the metal pentafluoride and hydrogen halide to the support can range from 1:100 to 3:10.

The present invention also contemplates the use of polymers, copolymers, interpolymers, crosspolymers, etc., as for example, diisobutylene and triisobutylene polymers, the codimer of normal butylenes and the like. These materials are broken down into smaller units which can then be alkylated according to the process of the present invention. The use of mixtures of two or more of the above-described feedstocks in envisioned for use in the present process.

Paraffinic hydrocarbon feedstocks that are suitable for use in the present invention include the aliphatic and cycloaliphatic hydrocarbons. The aliphatic hydrocarbons (straight and branched chain materials) contain 3 to 12 carbon atoms per molecule ($C_3$–$C_{12}$), preferably 4–12 carbon atoms ($C_4$–$C_{12}$), and may be exemplified by propane, n-butane, isobutane, pentanes, hexanes, heptanes, and the like. The cycloaliphatic hydrocarbons (napthenes) contain 5 to 15 carbon atoms per molecule, preferably 6 to 12 carbon atoms, and may be exemplified by methylcyclopentane, dimethylcyclopentane, ethylcyclohexane, n-pentylcyclohexane and the like.

It should be clearly understood that use of paraffinic hydrocarbon feedstocks having more than 12 carbon atoms per molecule, e.g., polymers, paraffinic waxes and the like, are contemplated in the present invention. However, such feedstocks may not be alkylated directly because paraffinic species having more than about 8 carbon atoms per molecule are less stable in a strong acid environment and will tend to break down to more stable, i.e. lower carbon number, reaction intermediates in the acid solution. The lower carbon number intermediates will then be alkylated according to the present invention to form the desired liquid product. It is believed that cycloaliphatic hydrocarbons will behave in a similar manner but at a slower reaction rate.

According to the present invention, a paraffinic feedstock containing smaller paraffins, i.e. $C_3$–$C_6$, preferably $C_4$–$C_6$ paraffins such as propane, n-butanes, isobutane, isopentanes, isohexanes or mixtures thereof, can undergo alkylation with larger paraffins, i.e. paraffins or a mixture of paraffins, i.e. paraffins or a mixture of paraffins having more than 6 carbon atoms, to ultimately form lower molecular weight materials. While not wishing to be bound by any particular theory, it is believed that the actual reaction involves initial isomerization of the larger paraffin followed by alkylation of the larger isomerized paraffin with the smaller paraffin followed by cleavage and information of primarily $C_4$ to $C_6$ isomerized paraffins. Thus, isobutane can undergo a paraffin alkylation reaction with a heptane to form pentanes and hexanes, or with an octane to form primarily pentanes and hexanes. Similarly, isopentane can be reacted with a heptane to form an equilibrium mixture of butanes and hexanes.

An excess of the smaller paraffin relative to the larger paraffin, should be maintained. Typically, the molar ratio of smaller paraffin to larger paraffin in the reaction zone should be in the range of from about 2:1 to about 100:1, preferably from about 3:1 to about 20:1. When normal or isobutane is used in excess of the stoichiometric amount required to react with the larger paraffin, the excess serves both as a solvent for the reaction and as a driving force for the equilibrium to favor the formation of $iC_5$ and $iC_6$ paraffins as the primary products.

Since the major portion of the product is isomerized $C_4$–$C_6$ paraffins, one embodiment of the present invention envisions the introduction of extraneous isomerizable feedstocks to the reaction zone, i.e., isomerizable feedstocks not formed during the alkylation reaction. Typical isomerizable feedstocks include acyclic and alicyclic aliphatic hydrocarbons having at least four carbon atoms that are converted to a product enriched in an isomer thereof. Typically, acyclic hydrocarbons having at least four carbon atoms, that is straight chain or branched chain paraffins having from about 4 to 10 atoms, preferably from about 4 to 8 carbon atoms, are converted to branched materials having higher octane ratings. Additionally, alicyclic hydrocarbons (naphthenes) having at least 6 carbon atoms, typically from 6 to about 50 carbon atoms, preferably 6 to 15 carbon atoms, can be converted to isomers thereof by contacting the same with hydrogen in the presence of the catalyst system described previously. Mixtures of acyclic and alicyclic hydrocarbons can be used as the process feedstock. In a typical commercial operation, a paraffin stream containing mixtures of various types of open chain and closed chain paraffins is used as the process feedstock. However, the feedstocks should be substantially free of aromatics.

Should the smaller paraffin reactant/solvent not be available for the alkylation reaction, they can be obtained by hydrocracking larger paraffins, e.g. the larger paraffin feedstock. Additional larger paraffins can then be added to effect the alkylation reaction.

The present catalyst system is particularly suited for use in refinery alkylation processes. The process of this invention contemplates the use of various refinery streams as feedstocks. For example, the smaller paraffin can be obtained from $C_5$–$C_6$ light virgin naphtha, while the larger paraffin can be obtained from virgin naphtha reformer feeds, cat naphtha raffinate, Fischer-Tropsch products, etc. Whatever their source, the feedstocks are preferably dried to control excess water buildup, i.e. about 0.5 to 15 wppm, preferably about 0.5 to 2 wppm of water before entering the reactor.

The amount of the aforementioned catalyst present during alkylation is not critical to the practice of the present invention. In general, the catalyst is present in catalytic amounts. The amount of larger paraffin contacted with the catalyst can range from about 0.1 to 10 parts by volume of paraffin per part by volume of catalyst present in the reaction mixture per hour. Preferably, the amount of larger paraffin present will range from 0.25 to 5.0 parts by volume per part by volume of the smaller paraffin present in the reaction mixture per hour. In addition, the volume percent of catalyst in the emulsion mixture; i.e., the liquid hydrocarbon plus catalyst, ranges from about 30 to about 85, preferably from about 50 to about 70. At any given point in time, it is preferred to have an excess of smaller paraffin relative to larger paraffin in the reaction mixture.

It is preferable that the alkylation process of the present invention be conducted in the presence of hydrogen. The hydrogen serves as a moderator for cracking reactions that might occur and will hydrogenate free intermediates, polymeric materials as well as other unsaturated materials, which might be formed during the reaction and, thus, be present in the acid phase and result in higher process selectivity. This also has the effect of increasing the life of the catalyst system. However, hydrogen is necessary to effect hydrocracking of the larger paraffins into smaller paraffins as mentioned above.

The amount of hydrogen present in the acid catalyst during alkylation is not critical, provided there is an amount sufficient to saturate alkylation sludge precursors, i.e. to saturate the intermediate products formed during the break-up of any polymers formed during alkylation. Amounts ranging from about 0.1 to about 5.0 wt. % based on hydrocarbon feed are sufficient although greater amounts may be used. The hydrogen may be present in the form of a hydrogen-containing gas which may be obtained from any number of sources including commercially available pure hydrogen, naphtha reformers, hydrogen plants, as well as the off-gases from any hydrotreating process or hydrogen donor organic molecules such as tetralin, methylcyclohexane, decalin, isobutane and the like. The term "hydrotreating process" is meant to include hydrofining, hydrocracking, hydrodesulfurization and the like or synthetic schemes in which hydrogen is a product. The hydrogen-containing gas may be pure or contain other gaseous materials such as light hydrocarbons ($C_1$–$C_8$), small amounts of both carbon monoxide and carbon dioxide and the like. Depending upon the nature of the feedstock and the alkylation conditions, some of the $C_1$–$C_8$ lighter hydrocarbons will alkylate to form additional liquid product. The hydrogen-containing gas may be introduced into the alkylation process alone or be mixed with the hydrocarbon feed prior to said introduction. Preferably the hydrogen-containing gas will be dry.

The process catalyst system is somewhat sensitive to impurities such as water. Therefore, the present alkylation process should be conducted in the absence of large amounts of moisture, and preferably under substantially anhydrous conditions, i.e. less than 3 wt. %, preferably less than about 1 wt. %, water, based on the metal pentafluoride component of the catalyst.

In general, the alkylation reaction temperatures will range from about $-100°$ to about $+100°$ C., preferably from about $-30°$ to about $+75°$ C., more preferably from about $-10°$ to about $+60°$ C. The temperature may be controlled in any convenient manner, for example by autorefrigeration using propane butanes or a hydrogen halide depending upon the composition of the reaction mixture. Autorefrigeration may be employed to remove the heat of reaction and/or lower the temperature of the reaction mixture.

The pressure at which the reaction is carried out will depend upon the feedstream being processed, the reaction diluent, the hydrogen purity (i.e. less hydrogen present will require increased pressure) as well as other process variables. In general, the pressure should be sufficient to maintain at least a portion of one of the catalyst components in the liquid phase. Preferably the present alkylation process will be conducted substantially in the liquid phase when using an unsupported catalyst system. This may be expressed in terms of hydrogen partial pressure which should be at least 0.1 atmospheres and may range from about 0.1 to about 100 atmospheres, preferably from about 0.1 to about 50 atmospheres and most preferably from about 0.3 to about 25 atmospheres. The total pressure may range from about 0.1 to about 150 atmospheres. The present alkylation process may be conducted in the presence of an inert atmosphere such as nitrogen. It is preferred that said alkylation be conducted in the substantial absence of an oxygen-containing gas; i.e. less than about 1 wt. percent oxygen based on the inert atmosphere.

In the present process, the reactants are contacted in the presence of a catalyst for a time sufficient to effect the degree of alkylation desired. In general, the contact time is subject to wide variation. The length of the contact time depends in part upon the temperature, the reactants used and the catalyst concentration employed. Typical contact times will range from about 0.05 seconds to several hours, preferably from about 0.05 seconds to about 2 hours, more preferably from about 1 minute to about 1 hour.

The alkylation process of the present invention may be conducted in a batch, intermittent or continuous type operation. Preferably, the invention is carried out in a continuous manner to minimize further reaction of the product or products formed. It has been generally established that in alkylation processes, the more intimate the contact between the feedstock and the catalyst the better the yield of saturated product obtained. Thus, the apparatus employed may be of a conventional nature and comprise a single reactor or multiple reactors equipped with efficient stirring devices such as mechanical agitators, turbomixers, jet mixers and the like. One or more reactants may be introduced into the reaction zone through dispersion devices such as jets of restricted internal diameter, porous thimbles, and the like. The hydrocarbon or paraffin-paraffin phase, the catalyst phase and the hydrogen-containing gas may be passed through one or more reactors in concurrent, cross-current, or countercurrent flow. After a sufficient period of time, unreacted reactants, partially deactivated catalyst, inhibitors and heavier products of the reaction may be separated from the desired alkylation product and from one another, such as by distillation, and returned in whole or in part to the alkylation zone. If desired, a portion of the partially deactivated catalyst can be regenerated or reactivated by any suitable treatment and returned to the alkylation process.

Reactions involving the use of the present catalyst system can be conducted in vessels fabricated from carbon steel provided that excessive temperatures are not used and provided further that the reaction system is maintained in a substantially anhydrous condition. Teflon, Carpenter 20 Cb-3 (Alloy 20) steel or Monel may be used in the fabrication of reaction equipment as well as aluminum-magnesium alloys, e.g., aluminum 5052, 6061 and the like.

In general, reaction and/or recovery schemes and apparatus employed in conjunction with prior art liquid acid catalyst systems can be used with the catalyst systems of the present invention. Examples of potentially applicable process techniques and apparatus are described in U.S. Pat. Nos. 2,433,944, 2,479,366, 2,701,184, 2,717,913, 2,775,636, 3,766,293, U.K. Pat. Nos. 543,046, 577,869, 713,806, 738,348, U.S. Pat. No. 803,458, U.K. Pat. Nos. 804,966, and 881,892, the disclosures of which are incorporated herein by reference.

Use of the present invention results in the production of an alkylate having more highly branched isomers that have a higher octane number than the hydrocarbon feedstocks. As such the alkylate product is particularly well suited for use as blending components for a refinery motor gasoline pool.

The following examples are presented to further illustrate the process of the present invention and are not intended to unduly restrict the limits of the claims appended hereto:

EXAMPLE 1

Into a 400 ml Hastelloy C Autoclave Engineer's stirred autoclave were placed tantalum pentafluoride (83 g, 0.30 mole), hydrogen fluoride (70 g, 3.50 mole) and isobutane (110 g, 1.90 mole). The reaction mixture was heated to 40° C. Normal octane (57 g, 0.50 mole) and hydrogen (0.03 mole) at about 30 psi were added to the reaction mixture which was being stirred at about 1000 rpm. Cold water was circulated through an internal cooling coil to help the thermostat maintain a temperature of 40° C. A sample was taken at 40° C. by connection of an evacuated 10 ml stainless steel cylinder to the reactor. When the valves connecting the two vessels were opened, product passed from the reactor through the dip stick into a 2 cc lock-hopper zone in which it was isolated and then passed into the smaller vessel by the difference in pressure. The sample was cooled to −70° C. and an aliquot of the vaporized liquid was analyzed on a Perkin Elmer 900 Gas Chromotograph with a flame ionization detector using a DC-200 capillary column at 50° C. After 30 minutes of reaction most of the hydrocarbon was removed and a fresh hydrocarbon charge was added. The reaction was repeated as above. After the second charge had reacted for 30 minutes, the entire procedure was repeated for a third time. The results indicate the following product distribution, excluding reactants:

| Product Distribution | After 30 minutes (Area %) | | |
| --- | --- | --- | --- |
| | Run 1 | Run 2 | Run 3 |
| propane | 2.7 | 0.6 | 0.5 |
| $C_5H_{12}$'s | 47.4 | 43.2 | 44.4 |
| % i-$C_5$ in $C_5H_{12}$'s | 83.5 | 81.2 | 83.1 |
| $C_6H_{14}$'s | 34.7 | 35.2 | 36.2 |
| % 2,2-$DMC_4$ in $C_6H_{14}$'s | 52.8 | 51.5 | 52.9 |
| $C_6+$ | 7.4 | 11.2 | 11.4 |

This example shows that isobutane reacts with normal octane to form a product (excluding reactants) containing primarily isopentanes and isohexanes.

EXAMPLE 2

Into a 300 ml Hastelloy C Autoclave Engineer's stirred autoclave were placed tantalum pentafluoride (55.2 g, 0.20 mole), hydrogen fluoride (40.0 g, 2.0 mole), isobutane (116 g, 2.0 mole) n-heptane (40 g, 0.4 mole) and hydrogen (∼5 psi, 0.004 mole). The reaction mixture was stirred at 1000 rpm and heated to 40° C. After about 30 minutes of reaction at 40° C., a sample was collected and analyzed as in Example 1 to give the following results, excluding reactants:

| Product Distribution | Area % |
|---|---|
| Pentanes | 63.7 |
| Hexanes | 29.10 |
| Heptanes | 7.2 |
| i-$C_5$ in $C_5H_{12}$'s | 82.7 |
| 2,2-$DMC_4$ in $C_6H_{14}$'s | 52.4 |

Example 2 shows that the present catalyst system is also highly active and selective to the formation of desirable high octane branched isomers via paraffin-paraffin alkylation.

EXAMPLE 3

Into a 400 ml Hastelloy C autoclave Engineer's stirred autoclave where placed tantalum pentafluoride (83g, 0.30 mole), hydrogen fluoride (60g, 3.0 mole). A mixture (35%, 150 ml composed of n-heptane (6.5%), n-octane (25.8%), n-nonane (41.9%), n-decane (12.9%) and n-undecane (12.9%) was diluted in isobutane (65%) to make a final mixture having a H/C ratio of 2.4. The reaction mixture was stirred at 1000 rpm and heated to 40° C. As in Example 1, three 30 minute recycles of feed were carried out over the same charge of catalyst and the products analyzed. The results indicated the following product distributions (including butanes):

| Product Distribution | After 30 Minutes (Area %) | | |
|---|---|---|---|
| | Run 1 | Run 2 | Run 3 |
| Propane | 1.2 | 3.2 | 0.8 |
| Butanes | 39.3 | 49.3 | 46.2 |
| Pentanes | 31.2 | 23.1 | 28.4 |
| Hexanes | 28.3 | 24.4 | 24.6 |
| % $C_3$-$C_6$ | 97.9 | 95.2 | 94.3 |
| % $C_7$-$C_{11}$ | 2.1 | 4.8 | 5.7 |

This Example shows that smaller paraffins (isobutane) is reacted with a mixture of larger paraffins ($C_7$-$C_{11}$) to form an alkylate (including isobutane) which contains primarily isopentanes and isohexanes.

EXAMPLE 4

Into a 400 ml Hastelloy C Autoclave Engineer's stirred autoclave were placed tantalum pentafluoride (138g, 0.5 mole) and hydrogen fluoride (100g, 5.0 mole). A mixture comprising n-pentane (25%), 2-methylpentane (22%), n-hexane (20%), cyclohexane (8%) and n-heptane (25%) was diluted in isobutane (110g, 1.9 mole) and also placed in the autoclave. The reaction mixture was stirred at 1650 rpm and heated to 40° C. at which time a sample was taken. Samples were then taken at various intervals thereafter. The total pressure was about 70 psig, with from 3 to 5 psig hydrogen being present. The samples were analyzed as in Example 1 and the following results obtained:

| Sample Time, min. | 0(20° C) | 0(40° C) | 7 | 13 | 20 | 30 |
|---|---|---|---|---|---|---|
| Product Distribution | | | | | | |
| $C_3$ | — | — | — | — | — | — |
| i-$C_4$ | — | — | — | — | — | — |
| n-$C_4$ | — | — | — | — | — | — |
| i-$C_5$ | 1.71 | 7.70 | 19.73 | 32.11 | 34.86 | 37.73 |
| n-$C_5$ | 18.00 | 11.85 | 4.78 | 6.46 | 7.51 | 9.38 |
| 2,2-$DMC_4$ | 6.86 | 10.64 | 25.40 | 25.88 | 24.62 | 22.70 |
| 2,3-$DMC_4$ and 2-$MC_5$ | 18.81 | 18.81 | 18.08 | 14.80 | 14.02 | 13.40 |
| 3-$MC_5$ | 6.32 | 6.46 | 5.95 | 4.79 | 4.67 | 4.54 |
| n-$C_6$ | 15.33 | 11.01 | 4.01 | 2.82 | 2.59 | 2.42 |
| MCP + 2,2 DMP | 0.99 | 2.78 | 2.14 | 2.14 | 2.29 | 2.34 |
| i-$C_7$+ | 24.03 | 23.46 | 15.41 | 9.67 | 9.27 | 7.50 |
| $CyC_6$ | 7.95 | 6.97 | 4.47 | 1.31 | 0.18 | — |
| Total (%) | 100.00 | 99.68 | 99.97 | 99.98 | 100.01 | 100.01 |
| Conversions | | | | | | |
| $C_4$— | — | — | — | — | — | — |
| $C_5H_{12}$'s | 19.71 | 19.55 | 24.51 | 38.57 | 42.37 | 47.11 |
| % i-$C_5$ in $C_5H_{12}$'s | 8.68 | 39.39 | 80.50 | 83.25 | 82.28 | 80.09 |
| $C_6H_{14}$'s | 47.32 | 46.92 | 53.44 | 48.29 | 45.90 | 43.06 |
| % 2,2-$DMC_4$ in $C_6H_{14}$'s | 14.50 | 22.68 | 47.53 | 53.59 | 53.64 | 52.72 |
| % n-$C_6$ in $C_6H_{14}$'s | 32.40 | 23.47 | 7.50 | 5.84 | 5.64 | 5.62 |
| % $C_5$'s in $C_5 + C_6 + C_7$ | 21.65 | 21.74 | 26.25 | 39.96 | 43.44 | 48.23 |
| % $C_6$'s in $C_5 + C_6 + C_7$ | 51.97 | 52.17 | 57.24 | 40.03 | 47.06 | 44.09 |
| % $C_7$ in $C_5 + C_6 + C_7$ | 26.39 | 26.09 | 16.51 | 10.02 | 9.50 | 7.68 |

This Example shows that $C_5/C_6$ isomerization and i-$C_4$/$C_7$ paraffin alkylation can be carried out simultaneously with the present catalyst system.

EXAMPLE 5

Into a 400 ml Hastelloy C Autoclave Engineer's stirred autoclave were placed tantalum pentafluoride (42.0g, 0.15 mole), hydrogen fluoride (60.0g, 3.0 mole) and n-butane (80.0g, 1.4 mole). In the first part of this experiment, the reaction mixture was heated to 40° C, stirred at 1000 rpm and allowed to react for one hour. A hydrocarbon sample taken after one hour and analyzed as above, indicated the following composition.

| Product Distribution | Composition (%) at 40° C | |
|---|---|---|
| | 0 Min. | 60 Min. |
| $C_3$ | 0.69 | 0.68 |
| i-$C_4$ | 1.13 | 1.56 |
| n-$C_4$ | 98.03 | 97.58 |

The result shows that little isomerization of n-butane to isobutane occurs at 40° C. n-Heptane (26.0g, 0.26 mole) was then pressured into the reactor. After twenty minutes of reaction a hydrocarbon sample was analyzed and indicated the following:

| Product Distribution | Composition (%) at 40° C | |
|---|---|---|
| | 0 Min | 20 Min. |
| $C_1$-$C_3$ | 0.0 | 5.3 |
| i-$C_4$ | 1.4 | 41.0 |
| n-$C_4$ | 73.8 | 29.6 |
| i-$C_5$ | 0.0 | 12.7 |
| n-$C_5$ | 0.0 | 2.4 |
| 2,2-$DMC_4$ | — | 3.9 |
| 2,3-$DMC_4$ + 2-$MC_5$ | — | 2.3 |

-continued

| Product Distribution | Composition (%) at 40° C | |
|---|---|---|
| | 0 Min | 20 Min. |
| 3-MC$_5$ | — | 0.8 |
| n-C$_6$ | — | 0.5 |
| n-C$_7$ | 23.4 | — |
| C$_7$H$_{16}$'s | 0.7 | 1.5 |
| % 2,2-DMC$_4$ in C$_6$H$_{14}$'s | — | 52.1 |
| % i-C$_4$ in C$_4$H$_{10}$'s | — | 58.1 |
| % i-C$_5$ in C$_5$H$_{12}$'s | — | 84.3 |
| % C$_4$H$_{10}$'s | 72.3 | 70.6 |
| % C$_5$H$_{12}$'s | 0.10 | 15.1 |
| % C$_6$H$_{14}$'s | — | 2.5 |
| % C$_7$H$_{16}$'s | 24.0 | 1.5 |

The results of this reaction clearly show that the paraffin alkylation reaction proceeds smoothly when n-butane is reacted with n-heptane using the catalyst system of the present invention at moderate reaction conditions to give primarily an iso-C$_4$/iso-C$_5$/iso-C$_6$ product of enhanced octane. The butane can be completely or partially recycled to the reaction zone.

When the hydrogen halide is hydrogen fluoride, temperature control in the alkylation zone can be maintained by vaporizing a portion of the C$_3$ paraffin, C$_4$ paraffin or mixtures thereof.

What is claimed is:

1. A process wherein a paraffinic feedstock comprising C$_3$–C$_6$ paraffinic hydrocarbons is reacted with larger paraffinic hydrocarbons having more than 6 carbon atoms under substantially anhydrous reaction conditions in the presence of hydrogen and a catalyst comprising a metal pentafluoride selected from the group consisting of tantalum pentafluoride, niobium pentafluoride and mixtures thereof and a hydrogen halide, to form a product containing primarily C$_4$–C$_6$ paraffins and having an octane number greater than that of the said feedstock.

2. The process of claim 1 wherein the molar ratio of hydrogen halide to metal pentafluoride is at least equimolar.

3. The process of claim 2 wherein the hydrogen halide is hydrogen fluoride.

4. The process of claim 1 wherein the molar ratio of said C$_3$–C$_6$ paraffinic hydrocarbons to said larger paraffinic hydrocarbons ranges from 2:1 to 100:1.

5. The process of claim 1 wherein said reaction occurs in the substantial absence of aromatic compounds.

6. The process of claim 1 wherein said alkylation occurs substantially in the liquid phase.

7. The process of claim 1 wherein said catalyst is supported on a solid carrier that is substantially inert to said hydrogen halide.

8. The process of claim 1 wherein sufficient hydrogen is present to maintain a hydrogen partial pressure of at least 0.1 atmosphere.

9. The process of claim 1 wherein an alicyclic hydrocarbon having at least six carbon atoms is included in the reaction.

10. The process of claim 1 wherein said C$_3$–C$_6$ paraffinic hydrocarbons are obtained by hydrocracking a portion of said larger paraffinic hydrocarbons.

11. A process which comprises reacting a paraffinic feedstock comprising C$_3$–C$_6$ hydrocarbons with paraffinic hydrocarbons having more than 6 carbon atoms under substantially anhydrous conditions in the presence of hydrogen and with a catalyst comprising a metal pentafluoride selected from the group consisting of tantalum pentafluoride, niobium pentafluoride and mixtures thereof, and hydrogen fluoride, wherein the ratio of said hydrogen fluoride to metal pentafluoride is at least equimolar, the reaction taking place substantially in the liquid phase, at a temperature ranging between about −100° and +100° C. and a hydrogen partial pressure of at least 0.1 atmosphere to form a product containing primarily C$_4$–C$_6$ paraffins and having an octane number greater than that of said feedstock.

12. The process of claim 11 wherein the molar ratio of said C$_3$–C$_6$ paraffinic hydrocarbons to said larger paraffinic hydrocarbons ranges from 3:1 to 20:1.

13. The process of claim 11 wherein the molar ratio of hydrogen fluoride to metal pentafluoride is at least 2:1.

14. The process of claim 11 wherein the paraffinic feedstock comprises a C$_4$–C$_6$ paraffinic hydrocarbon.

15. The process of claim 11 wherein said reaction occurs in the substantial absence of aromatic compounds.

16. The process of claim 11 wherein said temperature ranges between about −30° and +75° C.

17. The process of claim 11 wherein temperature control is maintained by vaporizing a portion of the C$_3$ paraffin, the C$_4$ paraffins or mixtures thereof during said reaction.

* * * * *